(12) United States Patent
Carty

(10) Patent No.: US 7,722,246 B1
(45) Date of Patent: May 25, 2010

(54) METHOD FOR DETERMINING THE THERMAL EXPANSION COEFFICIENT OF CERAMIC BODIES AND GLAZES

(76) Inventor: William M. Carty, 1482 Waterwells Rd., Alfred Station, NY (US) 14803

( * ) Notice: Subject to any disclaimer, the term of this patent is extended or adjusted under 35 U.S.C. 154(b) by 1393 days.

(21) Appl. No.: 11/110,586

(22) Filed: Apr. 20, 2005

(51) Int. Cl.
G01N 25/16 (2006.01)
(52) U.S. Cl. .............................. 374/44; 702/34; 374/5; 252/960
(58) Field of Classification Search ............. 374/43–45, 374/4–5, 47–57, 159, 187, 100, 137; 702/35, 702/40; 73/592; 252/964, 960
See application file for complete search history.

(56) References Cited

U.S. PATENT DOCUMENTS

| | | | | |
|---|---|---|---|---|
| 2,470,753 | A * | 5/1949 | Alban | 428/617 |
| 3,208,190 | A * | 9/1965 | Kakos et al. | 52/390 |
| 3,713,068 | A * | 1/1973 | Talmo | 338/2 |
| 4,103,002 | A * | 7/1978 | Hench et al. | 428/155 |
| 4,551,030 | A * | 11/1985 | Luukkala et al. | 374/5 |
| 4,767,672 | A * | 8/1988 | Fujinaka et al. | 428/446 |
| 4,826,326 | A * | 5/1989 | Reynolds et al. | 374/5 |
| 5,384,658 | A * | 1/1995 | Ohtake et al. | 359/707 |
| 5,435,889 | A * | 7/1995 | Dietrich | 216/63 |
| 5,473,513 | A * | 12/1995 | Quinn | 361/760 |
| 5,871,850 | A * | 2/1999 | Moriguchi et al. | 428/651 |
| 5,930,587 | A * | 7/1999 | Ryan | 438/14 |
| 5,980,988 | A * | 11/1999 | Ljungberg | 427/255.19 |
| 6,183,846 | B1 * | 2/2001 | Moriguchi et al. | 428/216 |
| 6,513,389 | B2 * | 2/2003 | Suresh et al. | 73/785 |
| 6,565,917 | B1 * | 5/2003 | Reddy et al. | 427/96.8 |
| 6,672,759 | B2 * | 1/2004 | Feger | 374/56 |
| 6,776,520 | B2 * | 8/2004 | Zhu | 374/55 |
| 7,147,367 | B2 * | 12/2006 | Balian et al. | 374/44 |
| 7,397,260 | B2 * | 7/2008 | Chanda et al. | 324/763 |
| 7,449,251 | B2 * | 11/2008 | Arikawa et al. | 428/689 |
| 2001/0005023 | A1 * | 6/2001 | Itoh et al. | 257/103 |
| 2002/0167988 | A1 * | 11/2002 | Zhu | 374/55 |
| 2004/0150310 | A1 * | 8/2004 | Azuma | 313/249 |
| 2007/0053784 | A1 * | 3/2007 | Muha et al. | 419/29 |
| 2007/0082131 | A1 * | 4/2007 | Doesburg et al. | 427/255.31 |
| 2007/0225153 | A1 * | 9/2007 | Reimanis et al. | 501/128 |
| 2008/0026160 | A1 * | 1/2008 | Taylor et al. | 427/454 |
| 2008/0160338 | A1 * | 7/2008 | Tanibuchi et al. | 428/627 |
| 2008/0193719 | A1 * | 8/2008 | Delsman et al. | 428/157 |

FOREIGN PATENT DOCUMENTS

JP 03128431 A * 5/1991
JP 02006064652 A * 3/2006

* cited by examiner

*Primary Examiner*—Gail Verbitsky
(74) *Attorney, Agent, or Firm*—C. John Brannon; Brannon & Sowers PC

(57) ABSTRACT

A method of measuring the coefficient of thermal expansion of a ceramic material, including the steps of applying a glaze to a substantially densified refractory body, wherein the coefficient of thermal expansion of either the glaze or the body is known, bonding the glaze to the body, putting the glaze insufficient tension to induce crazing, measuring the average distance between cracks in the crazed glaze; and determining the unknown coefficient of thermal expansion of the glaze or body.

21 Claims, 1 Drawing Sheet

METHOD FOR DETERMINING THE THERMAL EXPANSION COEFFICIENT OF CERAMIC BODIES AND GLAZES

CROSS-REFERENCE TO RELATED APPLICATIONS

This application claims priority to U.S. Provisional Patent Application Ser. No. 60/563,505, filed Apr. 19, 2004.

TECHNICAL FIELD OF THE INVENTION

The invention relates generally to the field of ceramic materials and, specifically, to a method and apparatus for determining coefficient of thermal expansion.

BACKGROUND OF THE INVENTION

Thermal expansion coefficients (C.T.E.s) are characteristics of ceramic and/or refractory bodies, glazes, and glasses that are critically important for many applications, both traditional and advanced. In the case of traditional ceramics, the thermal expansion mismatch between the body and its glaze is tailored to place the glaze layer into compression, thus strengthening both the body and the glaze. For glazed ceramic materials, the C.T.E. of the glaze is usually less than the C.T.E. of the underlying body such that on cooling, the glaze contracts less than the underlying body and is thus placed in compression. Correspondingly, the underlying body is placed in tension. In general, when a glaze is in compression, the glaze is considered to "fit" the body. If the glaze has a greater C.T.E. than the body, the glaze is placed in tension and will crack on cooling forming the glaze defect of crazing. It is often assumed that glaze thickness contributes to crazing but the data to date does not support this assertion. It has also been proposed that crazing is related to thermal shock, but this is similarly not supported by the data.

Measuring the thermal expansion coefficient, however, is difficult due to a variety of factors ranging from material heterogeneities to instrumental problems. Current technology requires a bar or rod sample that is placed in an instrument and the change in length of the sample measured as a function of temperature; the slope of that line is the C.T.E. Throughout the industry, it is widely accepted that measurement of the thermal expansion coefficient, while often repeatable within a specific lab, is often not reproducible between labs. This casts doubt on the reliability of the data and makes the global use of the data problematic. In addition, C.T.E. measurement equipment is often both slow and quite expensive. In other words, current C.T.E. testing is expensive, slow and unreliable. Thus, a need remains for a relatively cheap, quick and reliable technique for determining the thermal expansion coefficient of a ceramic material. The present invention addresses this need.

SUMMARY OF THE INVENTION

The present invention relates to an improved method and apparatus for measuring the coefficient of thermal expansion for ceramic glazes and bodies. One object of the present invention is to provide an improved method and apparatus for measuring the coefficient of thermal expansion for ceramic glazes and bodies. Related objects and advantages of the present invention will be apparent from the following description.

DESCRIPTION OF THE PREFERRED EMBODIMENTS

Figure 1:
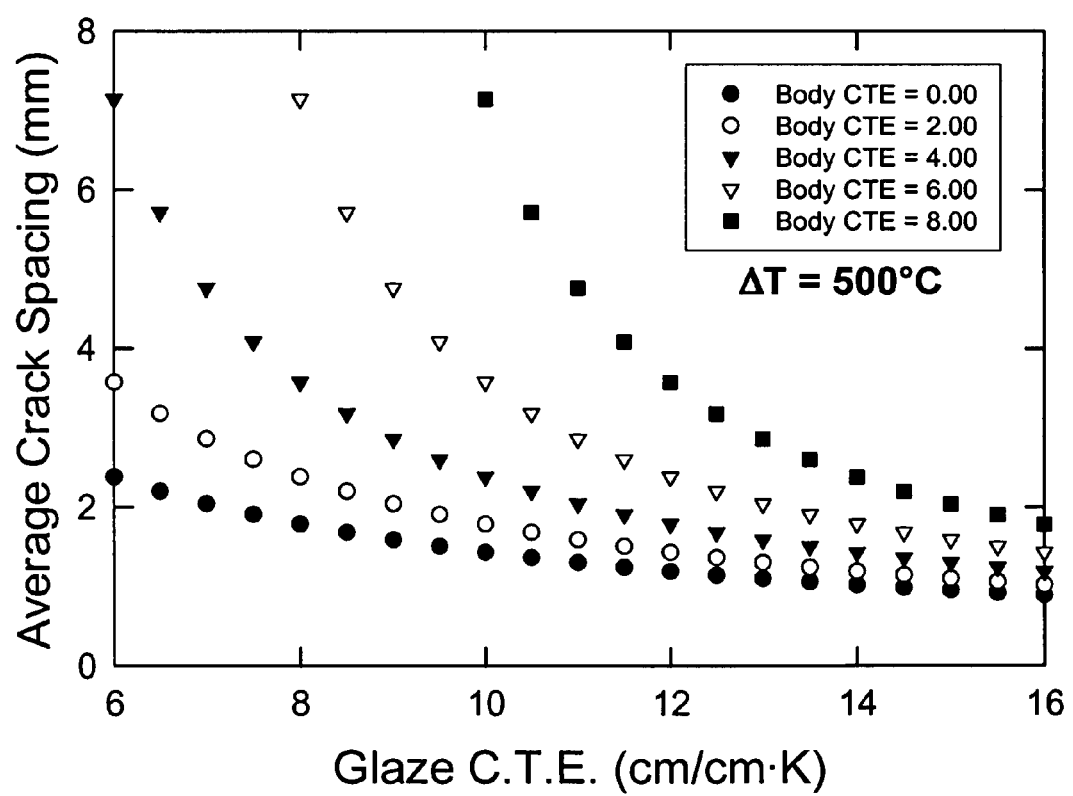
FIG. 1 is a plot of average crack spacing in a crazed glaze against glaze C.T.E. for bodies of various C.T.E.s and given a 500 degree Celsius differential.

For the purposes of promoting an understanding of the principles of the invention and presenting its currently understood best mode of operation, reference will now be made to the embodiments illustrated in the drawings and specific language will be used to describe the same. It will nevertheless be understood that no limitation of the scope of the invention is thereby intended, with such alterations and further modifications in the illustrated device and such further applications of the principles of the invention as illustrated therein being contemplated as would normally occur to one skilled in the art to which the invention relates.

In one embodiment of the present invention, the spacing of cracks in the glaze on a substrate body is used to determine the C.T.E. of either the body or the glaze when the C.T.E. of the other is a known quantity. The average separation distance between individual cracks in a crazed glaze is inversely related to the C.T.E. differential or mismatch between the body and glaze. As the magnitude of the C.T.E. mismatch increases (with the glaze in tension), the average spacing between individual cracks decreases. Likewise, as the C.T.E. mismatch decreases, cracks become rarer and are on average spaced farther apart. The use of standard bodies and standard glazes allow the C.T.E. of a candidate glaze or refractory body to be determined via a simple firing test, provided the glaze crazes. A lack of crazing is an indication of either a close C.T.E. match between the glaze and substrate over the relevant temperature range or an exceptionally tough glaze.

To Determine C.T.E. Mismatch Values:

The following equation relates the C.T.E. of the glaze and body and may be used to generate the C.T.E. differential data:

$$\alpha_G = \frac{(\sigma_{f,G})(10)}{E_G(T_{g,G} - T_a)x_c} + \alpha_B \quad (1)$$

where:
  $\alpha_G$≡C.T.E. of the glaze (cm/cm·K or cm·cm$^{-1}$·K$^{-1}$)
  $\alpha_B$≡C.T.E. of the body (cm·cm$^{-1}$·K$^{-1}$)
  $\sigma_{f,G}$≡Failure stress of the glaze (assumed to be 50 MPa)
  $E_G$≡Elastic modulus of the glaze (assumed to be 70 GPa)
  $T_{g,G}$≡glass transition temperature of the glaze (in ° C.)
  $T_a$≡ambient temperature after cooling (in ° C.)
  $x_c$≡spacing of the cracks in the glaze (in mm)

If the sample is cooled to 0° C. after heat treatment, the equation reduced to:

$$\alpha_G = \frac{(\sigma_{f,G})(10)}{E_G T_{g,G} x_c} + \alpha_B \quad (2)$$

Alternately, a table or plot of C.T.E. differential values versus average crack spacing for glazes on bodies fired to a specific temperature may be systematically prepared by applying glazes of predetermined C.T.E.s to bodies of predetermined C.T.E.'s and firing them to predetermined temperatures to generate a matrix of data points. The data may be measured, gathered, sorted and plotted and/or tabulated for later use.

Likewise, equation (1) may be rewritten as follows to calculate the C.T.E. of an unknown body:

$$\alpha_B = \frac{(\sigma_{f,G})(10)}{E_G T_{g,G} x_c} + \alpha_G \tag{3}$$

The following tables were generated from the above equations:

TABLE 1A

Predicted strain at $\Delta T = 400°$ C. in a glaze with an elastic modulus of 70 GPa ($E_G = 70$ GPa), a failure stress of 50 MPa ($\sigma_{G,f} = 50$ MPa), and a failure strain of 0.00071 ($\epsilon_{fail,G} = 0.00071$).
(If the strain value is zero or negative (<0.0) no cracks form in the glaze; these are noted via italics.)

| | | C.T.E.$_{Body}$ | | | | |
|---|---|---|---|---|---|---|
| | | 0.0 | 2.0 | 4.0 | 6.0 | 8.0 |
| | | | | $\epsilon_{Body}$ | | |
| | | 0.000 | 0.0008 | 0.0016 | 0.0024 | 0.0032 |
| C.T.E.$_{Glaze}$ | $\epsilon_{Glaze}$ | $\Delta\epsilon$ | $\Delta\epsilon$ | $\Delta\epsilon$ | $\Delta\epsilon$ | $\Delta\epsilon$ |
| 6.0 | 0.0024 | 0.00240 | 0.00160 | 0.00080 | *0.00000* | *-0.00080* |
| 6.5 | 0.0026 | 0.00260 | 0.00180 | 0.00100 | 0.00020 | *-0.00060* |
| 7.0 | 0.0028 | 0.00280 | 0.00200 | 0.00120 | 0.00040 | *-0.00040* |
| 7.5 | 0.003 | 0.00300 | 0.00220 | 0.00140 | 0.00060 | *-0.00020* |
| 8.0 | 0.0032 | 0.00320 | 0.00240 | 0.00160 | 0.00080 | *0.00000* |
| 8.5 | 0.0034 | 0.00340 | 0.00260 | 0.00180 | 0.00100 | 0.00020 |
| 9.0 | 0.0036 | 0.00360 | 0.00280 | 0.00200 | 0.00120 | 0.00040 |
| 9.5 | 0.0038 | 0.00380 | 0.00300 | 0.00220 | 0.00140 | 0.00060 |
| 10.0 | 0.004 | 0.00400 | 0.00320 | 0.00240 | 0.00160 | 0.00080 |
| 10.5 | 0.0042 | 0.00420 | 0.00340 | 0.00260 | 0.00180 | 0.00100 |
| 11.0 | 0.0044 | 0.00440 | 0.00360 | 0.00280 | 0.00200 | 0.00120 |
| 11.5 | 0.0046 | 0.00460 | 0.00380 | 0.00300 | 0.00220 | 0.00140 |
| 12.0 | 0.0048 | 0.00480 | 0.00400 | 0.00320 | 0.00240 | 0.00160 |
| 12.5 | 0.005 | 0.00500 | 0.00420 | 0.00340 | 0.00260 | 0.00180 |
| 13.0 | 0.0052 | 0.00520 | 0.00440 | 0.00360 | 0.00280 | 0.00200 |
| 13.5 | 0.0054 | 0.00540 | 0.00460 | 0.00380 | 0.00300 | 0.00220 |
| 14.0 | 0.0056 | 0.00560 | 0.00480 | 0.00400 | 0.00320 | 0.00240 |
| 14.5 | 0.0058 | 0.00580 | 0.00500 | 0.00420 | 0.00340 | 0.00260 |
| 15.0 | 0.006 | 0.00600 | 0.00520 | 0.00440 | 0.00360 | 0.00280 |
| 15.5 | 0.0062 | 0.00620 | 0.00540 | 0.00460 | 0.00380 | 0.00300 |
| 16.0 | 0.0064 | 0.00640 | 0.00560 | 0.00480 | 0.00400 | 0.00320 |

TABLE 1B

Predicted cracks per centimeter in a glaze under the conditions listed in TABLE 1A at a $\Delta T$ of 400° C.

| | C.T.E.$_{Body}$ | | | | |
|---|---|---|---|---|---|
| C.T.E.$_{Glaze}$ | 0.0 | 2.0 | 4.0 | 6.0 | 8.0 |
| 6.00 | 3.36000 | 2.24000 | 1.12000 | *0.00000* | *-1.12000* |
| 6.50 | 3.64000 | 2.52000 | 1.40000 | 0.28000 | *-0.84000* |
| 7.00 | 3.92000 | 2.80000 | 1.68000 | 0.56000 | *-0.56000* |
| 7.50 | 4.20000 | 3.08000 | 1.96000 | 0.84000 | *-0.28000* |
| 8.00 | 4.48000 | 3.36000 | 2.24000 | 1.12000 | *0.00000* |
| 8.50 | 4.76000 | 3.64000 | 2.52000 | 1.40000 | 0.28000 |
| 9.00 | 5.04000 | 3.92000 | 2.80000 | 1.68000 | 0.56000 |
| 9.50 | 5.32000 | 4.20000 | 3.08000 | 1.96000 | 0.84000 |
| 10.00 | 5.60000 | 4.48000 | 3.36000 | 2.24000 | 1.12000 |
| 10.50 | 5.88000 | 4.76000 | 3.64000 | 2.52000 | 1.40000 |
| 11.00 | 6.16000 | 5.04000 | 3.92000 | 2.80000 | 1.68000 |
| 11.50 | 6.44000 | 5.32000 | 4.20000 | 3.08000 | 1.96000 |
| 12.00 | 6.72000 | 5.60000 | 4.48000 | 3.36000 | 2.24000 |
| 12.50 | 7.00000 | 5.88000 | 4.76000 | 3.64000 | 2.52000 |
| 13.00 | 7.28000 | 6.16000 | 5.04000 | 3.92000 | 2.80000 |
| 13.50 | 7.56000 | 6.44000 | 5.32000 | 4.20000 | 3.08000 |
| 14.00 | 7.84000 | 6.72000 | 5.60000 | 4.48000 | 3.36000 |
| 14.50 | 8.12000 | 7.00000 | 5.88000 | 4.76000 | 3.64000 |
| 15.00 | 8.40000 | 7.28000 | 6.16000 | 5.04000 | 3.92000 |
| 15.50 | 8.68000 | 7.56000 | 6.44000 | 5.32000 | 4.20000 |
| 16.00 | 8.96000 | 7.84000 | 6.72000 | 5.60000 | 4.48000 |

TABLE 1C

Predicted average glaze crack spacing, in mm, for the conditions listed in TABLE 1A at a $\Delta T$ of 400° C.

| | C.T.E.$_{Body}$ | | | | |
|---|---|---|---|---|---|
| C.T.E.$_{Glaze}$ | 0.0 | 2.0 | 4.0 | 6.0 | 8.0 |
| 6.00 | 2.98 | 4.46 | 8.93 | no | no |
| 6.50 | 2.75 | 3.97 | 7.14 | 35.71 | no |
| 7.00 | 2.55 | 3.57 | 5.95 | 17.86 | no |
| 7.50 | 2.38 | 3.25 | 5.10 | 11.90 | no |
| 8.00 | 2.23 | 2.98 | 4.46 | 8.93 | no |
| 8.50 | 2.10 | 2.75 | 3.97 | 7.14 | 35.71 |
| 9.00 | 1.98 | 2.55 | 3.57 | 5.95 | 17.86 |
| 9.50 | 1.88 | 2.38 | 3.25 | 5.10 | 11.90 |
| 10.00 | 1.79 | 2.23 | 2.98 | 4.46 | 8.93 |
| 10.50 | 1.70 | 2.10 | 2.75 | 3.97 | 7.14 |
| 11.00 | 1.62 | 1.98 | 2.55 | 3.57 | 5.95 |
| 11.50 | 1.55 | 1.88 | 2.38 | 3.25 | 5.10 |
| 12.00 | 1.49 | 1.79 | 2.23 | 2.98 | 4.46 |
| 12.50 | 1.43 | 1.70 | 2.10 | 2.75 | 3.97 |
| 13.00 | 1.37 | 1.62 | 1.98 | 2.55 | 3.57 |
| 13.50 | 1.32 | 1.55 | 1.88 | 2.38 | 3.25 |
| 14.00 | 1.28 | 1.49 | 1.79 | 2.23 | 2.98 |
| 14.50 | 1.23 | 1.43 | 1.70 | 2.10 | 2.75 |
| 15.00 | 1.19 | 1.37 | 1.62 | 1.98 | 2.55 |
| 15.50 | 1.15 | 1.32 | 1.55 | 1.88 | 2.38 |
| 16.00 | 1.12 | 1.28 | 1.49 | 1.79 | 2.23 |

TABLE 2A

Predicted strain at $\Delta T = 500°$ C. in a glaze with an elastic modulus of 70 GPa ($E_G = 70$ GPa), a failure stress of 50 MPa ($\sigma_{G,f} = 50$ MPa), and a failure strain of 0.00071 ($\epsilon_{fail,G} = 0.00071$). (If the strain value is zero or negative (<0.0) no cracks form in the glaze; these are noted via italics.)

| | | C.T.E.$_{Body}$ | | | | |
|---|---|---|---|---|---|---|
| | | 0.0 | 2.0 | 4.0 | 6.0 | 8.0 |
| | | | | $\epsilon_{Body}$ | | |
| | | 0.000 | 0.001 | 0.002 | 0.003 | 0.004 |
| C.T.E.$_{Glaze}$ | $\epsilon_{Glaze}$ | $\Delta\epsilon$ | $\Delta\epsilon$ | $\Delta\epsilon$ | $\Delta\epsilon$ | $\Delta\epsilon$ |
| 6.0 | 0.003 | 0.00300 | 0.00200 | 0.00100 | *0.00000* | *-0.00100* |
| 6.5 | 0.00325 | 0.00325 | 0.00225 | 0.00125 | 0.00025 | *-0.00075* |
| 7.0 | 0.0035 | 0.00350 | 0.00250 | 0.00150 | 0.00050 | *-0.00050* |
| 7.5 | 0.00375 | 0.00375 | 0.00275 | 0.00175 | 0.00075 | *-0.00025* |
| 8.0 | 0.004 | 0.00400 | 0.00300 | 0.00200 | 0.00100 | *0.00000* |
| 8.5 | 0.00425 | 0.00425 | 0.00325 | 0.00225 | 0.00125 | 0.00025 |
| 9.0 | 0.0045 | 0.00450 | 0.00350 | 0.00250 | 0.00150 | 0.00050 |

TABLE 2A-continued

Predicted strain at ΔT = 500° C. in a glaze with an elastic modulus of 70 GPa ($E_G$ = 70 GPa), a failure stress of 50 MPa ($\sigma_{G,f}$ = 50 MPa), and a failure strain of 0.00071 ($\epsilon_{fail,G}$ = 0.00071). (If the strain value is zero or negative (<0.0) no cracks form in the glaze; these are noted via italics.)

| | | C.T.E.$_{Body}$ | | | | |
|---|---|---|---|---|---|---|
| | | 0.0 | 2.0 | 4.0 | 6.0 | 8.0 |
| | | $\epsilon_{Body}$ | | | | |
| | | 0.000 | 0.001 | 0.002 | 0.003 | 0.004 |
| C.T.E.$_{Glaze}$ | $\epsilon_{Glaze}$ | Δε | Δε | Δε | Δε | Δε |
| 9.5 | 0.00475 | 0.00475 | 0.00375 | 0.00275 | 0.00175 | 0.00075 |
| 10.0 | 0.005 | 0.00500 | 0.00400 | 0.00300 | 0.00200 | 0.00100 |
| 10.5 | 0.00525 | 0.00525 | 0.00425 | 0.00325 | 0.00225 | 0.00125 |
| 11.0 | 0.0055 | 0.00550 | 0.00450 | 0.00350 | 0.00250 | 0.00150 |
| 11.5 | 0.00575 | 0.00575 | 0.00475 | 0.00375 | 0.00275 | 0.00175 |
| 12.0 | 0.006 | 0.00600 | 0.00500 | 0.00400 | 0.00300 | 0.00200 |
| 12.5 | 0.00625 | 0.00625 | 0.00525 | 0.00425 | 0.00325 | 0.00225 |
| 13.0 | 0.0065 | 0.00650 | 0.00550 | 0.00450 | 0.00350 | 0.00250 |
| 13.5 | 0.00675 | 0.00675 | 0.00575 | 0.00475 | 0.00375 | 0.00275 |
| 14.0 | 0.007 | 0.00700 | 0.00600 | 0.00500 | 0.00400 | 0.00300 |
| 14.5 | 0.00725 | 0.00725 | 0.00625 | 0.00525 | 0.00425 | 0.00325 |
| 15.0 | 0.0075 | 0.00750 | 0.00650 | 0.00550 | 0.00450 | 0.00350 |
| 15.5 | 0.00775 | 0.00775 | 0.00675 | 0.00575 | 0.00475 | 0.00375 |
| 16.0 | 0.008 | 0.00800 | 0.00700 | 0.00600 | 0.00500 | 0.00400 |

TABLE 2B

Predicted cracks per centimeter in a glaze under the conditions listed in TABLE 2A at a ΔT of 500° C.

| | C.T.E.$_{Body}$ | | | | |
|---|---|---|---|---|---|
| C.T.E.$_{Glaze}$ | 0.0 | 2.0 | 4.0 | 6.0 | 8.0 |
| 6.00 | 4.20000 | 2.80000 | 1.40000 | *0.00000* | *−1.40000* |
| 6.50 | 4.55000 | 3.15000 | 1.75000 | 0.35000 | *−1.05000* |
| 7.00 | 4.90000 | 3.50000 | 2.10000 | 0.70000 | *−0.70000* |
| 7.50 | 5.25000 | 3.85000 | 2.45000 | 1.05000 | *−0.35000* |
| 8.00 | 5.60000 | 4.20000 | 2.80000 | 1.40000 | *0.00000* |
| 8.50 | 5.95000 | 4.55000 | 3.15000 | 1.75000 | 0.35000 |
| 9.00 | 6.30000 | 4.90000 | 3.50000 | 2.10000 | 0.70000 |
| 9.50 | 6.65000 | 5.25000 | 3.85000 | 2.45000 | 1.05000 |
| 10.00 | 7.00000 | 5.60000 | 4.20000 | 2.80000 | 1.40000 |
| 10.50 | 7.35000 | 5.95000 | 4.55000 | 3.15000 | 1.75000 |
| 11.00 | 7.70000 | 6.30000 | 4.90000 | 3.50000 | 2.10000 |
| 11.50 | 8.05000 | 6.65000 | 5.25000 | 3.85000 | 2.45000 |
| 12.00 | 8.40000 | 7.00000 | 5.60000 | 4.20000 | 2.80000 |
| 12.50 | 8.75000 | 7.35000 | 5.95000 | 4.55000 | 3.15000 |
| 13.00 | 9.10000 | 7.70000 | 6.30000 | 4.90000 | 3.50000 |
| 13.50 | 9.45000 | 8.05000 | 6.65000 | 5.25000 | 3.85000 |
| 14.00 | 9.80000 | 8.40000 | 7.00000 | 5.60000 | 4.20000 |
| 14.50 | 10.15000 | 8.75000 | 7.35000 | 5.95000 | 4.55000 |
| 15.00 | 10.50000 | 9.10000 | 7.70000 | 6.30000 | 4.90000 |
| 15.50 | 10.85000 | 9.45000 | 8.05000 | 6.65000 | 5.25000 |
| 16.00 | 11.20000 | 9.80000 | 8.40000 | 7.00000 | 5.60000 |

TABLE 2C

Predicted average glaze crack spacing, in mm, for the conditions listed in TABLE 2A at a ΔT of 500° C.

| | C.T.E.$_{Body}$ | | | | |
|---|---|---|---|---|---|
| C.T.E.$_{Glaze}$ | 0.0 | 2.0 | 4.0 | 6.0 | 8.0 |
| 6.00 | 2.38 | 3.57 | 7.14 | no | no |
| 6.50 | 2.20 | 3.17 | 5.71 | 28.57 | no |
| 7.00 | 2.04 | 2.86 | 4.76 | 14.29 | no |
| 7.50 | 1.90 | 2.60 | 4.08 | 9.52 | no |
| 8.00 | 1.79 | 2.38 | 3.57 | 7.14 | no |

TABLE 2C-continued

Predicted average glaze crack spacing, in mm, for the conditions listed in TABLE 2A at a ΔT of 500° C.

| | C.T.E.$_{Body}$ | | | | |
|---|---|---|---|---|---|
| C.T.E.$_{Glaze}$ | 0.0 | 2.0 | 4.0 | 6.0 | 8.0 |
| 8.50 | 1.68 | 2.20 | 3.17 | 5.71 | 28.57 |
| 9.00 | 1.59 | 2.04 | 2.86 | 4.76 | 14.29 |
| 9.50 | 1.50 | 1.90 | 2.60 | 4.08 | 9.52 |
| 10.00 | 1.43 | 1.79 | 2.38 | 3.57 | 7.14 |
| 10.50 | 1.36 | 1.68 | 2.20 | 3.17 | 5.71 |
| 11.00 | 1.30 | 1.59 | 2.04 | 2.86 | 4.76 |
| 11.50 | 1.24 | 1.50 | 1.90 | 2.60 | 4.08 |
| 12.00 | 1.19 | 1.43 | 1.79 | 2.38 | 3.57 |
| 12.50 | 1.14 | 1.36 | 1.68 | 2.20 | 3.17 |
| 13.00 | 1.10 | 1.30 | 1.59 | 2.04 | 2.86 |
| 13.50 | 1.06 | 1.24 | 1.50 | 1.90 | 2.60 |
| 14.00 | 1.02 | 1.19 | 1.43 | 1.79 | 2.38 |
| 14.50 | 0.99 | 1.14 | 1.36 | 1.68 | 2.20 |
| 15.00 | 0.95 | 1.10 | 1.30 | 1.59 | 2.04 |
| 15.50 | 0.92 | 1.06 | 1.24 | 1.50 | 1.90 |
| 16.00 | 0.89 | 1.02 | 1.19 | 1.43 | 1.79 |

TABLE 3A

Predicted strain at ΔT = 600° C. in a glaze with an elastic modulus of 70 GPa ($E_G$ = 70 GPa), a failure stress of 50 MPa ($\sigma_{G,f}$ = 50 MPa), and a failure strain of 0.00071 ($\epsilon_{fail,G}$ = 0.00071). (If the strain value is zero or negative (<0.0) no cracks form in the glaze; these are noted via italics.)

| | | C.T.E.$_{Body}$ | | | | |
|---|---|---|---|---|---|---|
| | | 0.0 | 2.0 | 4.0 | 6.0 | 8.0 |
| | | $\epsilon_{Body}$ | | | | |
| | | 0.000 | 0.0012 | 0.0024 | 0.0036 | 0.0048 |
| C.T.E.$_{Glaze}$ | $\epsilon_{Glaze}$ | Δε | Δε | Δε | Δε | Δε |
| 6.0 | 0.0036 | 0.00360 | 0.00240 | 0.00120 | *0.00000* | *−0.00120* |
| 6.5 | 0.0039 | 0.00390 | 0.00270 | 0.00150 | 0.00030 | *−0.00090* |
| 7.0 | 0.0042 | 0.00420 | 0.00300 | 0.00180 | 0.00060 | *−0.00060* |
| 7.5 | 0.0045 | 0.00450 | 0.00330 | 0.00210 | 0.00090 | *−0.00030* |
| 8.0 | 0.0048 | 0.00480 | 0.00360 | 0.00240 | 0.00120 | *0.00000* |
| 8.5 | 0.0051 | 0.00510 | 0.00390 | 0.00270 | 0.00150 | 0.00030 |
| 9.0 | 0.0054 | 0.00540 | 0.00420 | 0.00300 | 0.00180 | 0.00060 |
| 9.5 | 0.0057 | 0.00570 | 0.00450 | 0.00330 | 0.00210 | 0.00090 |
| 10.0 | 0.006 | 0.00600 | 0.00480 | 0.00360 | 0.00240 | 0.00120 |
| 10.5 | 0.0063 | 0.00630 | 0.00510 | 0.00390 | 0.00270 | 0.00150 |
| 11.0 | 0.0066 | 0.00660 | 0.00540 | 0.00420 | 0.00300 | 0.00180 |
| 11.5 | 0.0069 | 0.00690 | 0.00570 | 0.00450 | 0.00330 | 0.00210 |
| 12.0 | 0.0072 | 0.00720 | 0.00600 | 0.00480 | 0.00360 | 0.00240 |
| 12.5 | 0.0075 | 0.00750 | 0.00630 | 0.00510 | 0.00390 | 0.00270 |
| 13.0 | 0.0078 | 0.00780 | 0.00660 | 0.00540 | 0.00420 | 0.00300 |
| 13.5 | 0.0081 | 0.00810 | 0.00690 | 0.00570 | 0.00450 | 0.00330 |
| 14.0 | 0.0084 | 0.00840 | 0.00720 | 0.00600 | 0.00480 | 0.00360 |
| 14.5 | 0.0087 | 0.00870 | 0.00750 | 0.00630 | 0.00510 | 0.00390 |
| 15.0 | 0.009 | 0.00900 | 0.00780 | 0.00660 | 0.00540 | 0.00420 |
| 15.5 | 0.0093 | 0.00930 | 0.00810 | 0.00690 | 0.00570 | 0.00450 |
| 16.0 | 0.0096 | 0.00960 | 0.00840 | 0.00720 | 0.00600 | 0.00480 |

TABLE 3B

Predicted cracks per centimeter in a glaze under the conditions listed in TABLE 3A at a ΔT of 600° C.

| | C.T.E.$_{Body}$ | | | | |
|---|---|---|---|---|---|
| C.T.E.$_{Glaze}$ | 0.0 | 2.0 | 4.0 | 6.0 | 8.0 |
| 6.00 | 5.04000 | 3.36000 | 1.68000 | *0.00000* | *−1.68000* |
| 6.50 | 5.46000 | 3.78000 | 2.10000 | 0.42000 | *−1.26000* |
| 7.00 | 5.88000 | 4.20000 | 2.52000 | 0.84000 | *−0.84000* |

TABLE 3B-continued

Predicted cracks per centimeter in a glaze under the
conditions listed in TABLE 3A at a ΔT of 600° C.

| | C.T.E.$_{Body}$ | | | | |
|---|---|---|---|---|---|
| C.T.E.$_{Glaze}$ | 0.0 | 2.0 | 4.0 | 6.0 | 8.0 |
| 7.50 | 6.30000 | 4.62000 | 2.94000 | 1.26000 | *-0.42000* |
| 8.00 | 6.72000 | 5.04000 | 3.36000 | 1.68000 | *0.00000* |
| 8.50 | 7.14000 | 5.46000 | 3.78000 | 2.10000 | 0.42000 |
| 9.00 | 7.56000 | 5.88000 | 4.20000 | 2.52000 | 0.84000 |
| 9.50 | 7.98000 | 6.30000 | 4.62000 | 2.94000 | 1.26000 |
| 10.00 | 8.40000 | 6.72000 | 5.04000 | 3.36000 | 1.68000 |
| 10.50 | 8.82000 | 7.14000 | 5.46000 | 3.78000 | 2.10000 |
| 11.00 | 9.24000 | 7.56000 | 5.88000 | 4.20000 | 2.52000 |
| 11.50 | 9.66000 | 7.98000 | 6.30000 | 4.62000 | 2.94000 |
| 12.00 | 10.08000 | 8.40000 | 6.72000 | 5.04000 | 3.36000 |
| 12.50 | 10.50000 | 8.82000 | 7.14000 | 5.46000 | 3.78000 |
| 13.00 | 10.92000 | 9.24000 | 7.56000 | 5.88000 | 4.20000 |
| 13.50 | 11.34000 | 9.66000 | 7.98000 | 6.30000 | 4.62000 |
| 14.00 | 11.76000 | 10.08000 | 8.40000 | 6.72000 | 5.04000 |
| 14.50 | 12.18000 | 10.50000 | 8.82000 | 7.14000 | 5.46000 |
| 15.00 | 12.60000 | 10.92000 | 9.24000 | 7.56000 | 5.88000 |
| 15.50 | 13.02000 | 11.34000 | 9.66000 | 7.98000 | 6.30000 |
| 16.00 | 13.44000 | 11.76000 | 10.08000 | 8.40000 | 6.72000 |

TABLE 3C

Predicted average glaze crack spacing, in mm, for
the conditions listed in TABLE 3A at a ΔT of 600° C.

| | C.T.E.$_{Body}$ | | | | |
|---|---|---|---|---|---|
| C.T.E.$_{Glaze}$ | 0.0 | 2.0 | 4.0 | 6.0 | 8.0 |
| 6.00 | 1.98 | 2.98 | 5.95 | no | no |
| 6.50 | 1.83 | 2.65 | 4.76 | 23.81 | no |
| 7.00 | 1.70 | 2.38 | 3.97 | 11.90 | no |
| 7.50 | 1.59 | 2.16 | 3.40 | 7.94 | no |
| 8.00 | 1.49 | 1.98 | 2.98 | 5.95 | no |
| 8.50 | 1.40 | 1.83 | 2.65 | 4.76 | 23.81 |
| 9.00 | 1.32 | 1.70 | 2.38 | 3.97 | 11.90 |
| 9.50 | 1.25 | 1.59 | 2.16 | 3.40 | 7.94 |
| 10.00 | 1.19 | 1.49 | 1.98 | 2.98 | 5.95 |
| 10.50 | 1.13 | 1.40 | 1.83 | 2.65 | 4.76 |
| 11.00 | 1.08 | 1.32 | 1.70 | 2.38 | 3.97 |
| 11.50 | 1.04 | 1.25 | 1.59 | 2.16 | 3.40 |
| 12.00 | 0.99 | 1.19 | 1.49 | 1.98 | 2.98 |
| 12.50 | 0.95 | 1.13 | 1.40 | 1.83 | 2.65 |
| 13.00 | 0.92 | 1.08 | 1.32 | 1.70 | 2.38 |
| 13.50 | 0.88 | 1.04 | 1.25 | 1.59 | 2.16 |
| 14.00 | 0.85 | 0.99 | 1.19 | 1.49 | 1.98 |
| 14.50 | 0.82 | 0.95 | 1.13 | 1.40 | 1.83 |
| 15.00 | 0.79 | 0.92 | 1.08 | 1.32 | 1.70 |
| 15.50 | 0.77 | 0.88 | 1.04 | 1.25 | 1.59 |
| 16.00 | 0.74 | 0.85 | 0.99 | 1.19 | 1.49 |

Determining Craze Spacing Separation Distance:

Crazing is a random phenomenon generating cracks of orientation often independent of the orientation of the substrate. The spacing of the craze marks follows a statistical distribution. There are a number of methods for determining the spacing separation distance, including a simple line-intercept method in which a line is drawn across the sample at random and the number of cracks that intercept that line be counted and the length of the line divided by the number of cracks to obtain an average separation distance. For this technique, several lines are typically measured to generate better statistical significance. Alternately, a grid may be superimposed over the body and the number of cracks within a grid element used to obtain a average crack density and therefore a crack separation distance. Since the tiles are typically substantially flat, an automated technique, such as computer aided image analysis or the like, may be used to measure the craze spacing distances and calculate the unknown average crack separation distance and, eventually, the unknown C.T.E.

Compensating for Delayed Crazing:

In some systems, particularly those in which the C.T.E. mismatch is small, crazing is often delayed, occurring with time due to interaction of the glaze with the environment (usually due to the attack of the glaze by water vapor). In these cases, it is advantageous to use an autoclave to accelerate the glaze attack and to ensure that the glaze has reached a steady-state prior to the measurement of the craze spacings. The standard autoclave testing cycle is proposed.

Determination of the C.T.E. of a Glaze

Many conventional glazes fit refractory bodies well over certain temperature ranges. However, in cases where the C.T.E. of a glaze is unknown, the instant technique is useful for the investigation of an unknown glaze C.T.E. when the C.T.E. of the body and the C.T.E. of the glaze are substantially dissimilar (i.e., the C.T.E.'s of the body and the glaze do not fit). In the instant technique, the glaze is typically placed in tension to allow crazing to occur. At least one and, more typically, a plurality of standard bodies are prepared. Each standard body has a known and relatively low C.T.E.; if a plurality of standard bodies are prepared as a test set or series, each body is typically characterized by a different C.T.E. value. More typically, a series of standard bodies is prepared, each body having a different predetermined and relatively low C.T.E. such that the series spans both C.T.E. and maturation temperature, allowing accommodation of a wide range of glaze C.T.E.'s.

The low expansion standard reference series bodies are typically composed of petalite (a lithium feldspar), quartz, and china clay (although any commercial ceramic-grade clay can be used). Alternately, other convenient compositions having like C.T.E. properties may be selected. The reference bodies typically have a range of maturation temperatures, such as of cone 04 (1060° C.), cone 1 (1154° C.), cone 4 (1186° C.), and cone 10 (1305° C.), based on Orton Standard Pyrometric Cone designations. In cases where the reference body is pre-fired prior to the application of the glaze, it is important for the reference body not be over-fired at the glaze maturation temperature. For petalite-quartz-china clay bodies, the ratio of the raw materials will determine the thermal expansion coefficient of each resultant standard body in the series. Typically, a second set of test bodies is provided based on a standard stoneware or porcelain body composition (triaxial body formulation based on potash feldspar, quartz, and clay). The C.T.E. of each triaxial body in the second set is controlled by the amount of free quartz remaining in the body after firing, thus the thermal expansion of the body will change with temperature. Typically, a temperature correction chart is provided to allow for the initial firing temperature to be appropriately incorporated.

The reference and triaxial bodies are typically formed into regular shapes, such as 1"×2" tiles of thickness ¼", either by dry pressing or by another conventional ceramic forming technique. More typically, the bodies are fired (still more typically, bisqued fired) such that they are at least partially densified, and more typically completely densified, prior to use. Substantially complete densification of the bodies minimizes later body-glaze interactions. Typically, the bodies are fired at temperatures ranging from 950° to 1150° C.

Candidate glazes are applied to the densified standard test bodies/tiles through conventional application techniques (spraying, dipping, etc.), dried appropriately, and then refired to the glaze maturation temperature. After glazing and refiring, the samples are typically cooled and then evaluated to determine the presence and spacing of the glaze crazing marks. Since the C.T.E. of the body is known, the C.T.E. of the glaze may be determined from the spacing and/or pattern of the crazing marks. This may be accomplished counting the cracks intersecting a line of a predetermined length, by counting the cracks lying in a predetermined area, or the like and then performing a calculation or manually consulting a table or plot of craze spacing versus C.T.E. differential or mismatch. (See Tables 1A-3C and FIG. 1). Alternately, the process may be partially or even completely automated. The C.T.E. mismatch (the difference between body and glaze C.T.E.) is thus determined and, by arithmetically combining the C.T.E. of the body with the C.T.E. differential, the glaze C.T.E. is determined.

Determination of the C.T.E. of a Body:

A series of standard glaze compositions with predetermined and relatively high C.T.E. values is typically supplied for the C.T.E. characterization of candidate refractory or ceramic bodies. Each standard glaze composition is applied to the test body in the conventional fashion as addressed above. Several glazes may be applied to the test body, each applied in different, discrete locations. Alternately, a series of test bodies of identical composition may be used to each host one or more different glazes. The glazed candidate body/bodies is/are then fired and allowed to cool and the craze. The craze spacings for each respective test glaze composition are measured and quantified. The C.T.E. of the test body composition is determined by first determining the differential or mismatch between the body and glaze C.T.E.'s. This is done by calculation or by consulting tabulated or plotted data of craze spacing versus C.T.E. mismatch. Typically, a series of high and low C.T.E. glazes of predetermined C.T.E. values is provided such that a broad range of body compositions (and, thus, C.T.E.'s) may be accommodated and measured. Once the C.T.E. differential is determined, the body C.T.E. may be easily calculated as the difference between a particular glaze C.T.E. and the differential associated with that particular glaze C.T.E.

The technique applies independently of body shape. Typically, the craze spacings should be on the order of 5 mm to facilitate ease of measurements. More typically, as outlined above, several standard glazes are provided spanning a range of C.T.E. values.

While the invention has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the invention are desired to be protected.

What is claimed is:

1. A method of determining the coefficient of thermal expansion of a glaze or a refractory body, comprising:
    a) applying a glaze to the refractory body, wherein the refractory body is a substantially densified refractory body, wherein the glaze is characterized by a known elastic modulus, wherein the glaze is characterized by a known failure stress, wherein the glaze is characterized by a known glass transition temperature, and wherein the coefficient of thermal expansion of one of the glaze or the refractory body is known and the coefficient of the other of the glaze or the refractory body is unknown;
    b) bonding the glaze to the refractory body;
    c) putting the glaze into sufficient tension to induce crazing and to create cracks;
    d) measuring the average distance between cracks in the crazed glaze; and
    e) determining the unknown coefficient of thermal expansion of the glaze or refractory body according to the relationship wherein the difference between the known and unknown coefficients of thermal expansion is proportional to the failure stress of the glaze divided by the product of the elastic modulus of the glaze, the distance between the cracks in the crazed glaze, and the difference between the glass transition temperature of the glaze and the ambient temperature.

2. The method of claim 1 wherein step e) further includes the substeps of:
    e1) determining the thermal expansion differential between the glaze and the refractory body; and
    e2) arithmetically determining unknown coefficient of thermal expansion from the thermal expansion differential and the known coefficient of thermal expansion;
    wherein the thermal expansion differential and the coefficient of thermal expansion of the body sum to yield the coefficient of thermal expansion of the glaze.

3. The method of claim 1 wherein step e) includes calculating the unknown coefficient of thermal expansion from the known coefficient of thermal expansion, the firing temperature, and the average crack-to-crack distance.

4. The method of claim 1 wherein the glaze has a known coefficient of thermal expansion and the refractory body has an unknown coefficient of thermal expansion; and wherein step c) includes firing the glazed body to a first predetermined temperature.

5. The method of claim 4 wherein step e) further includes the substeps of:
    e1) determining the thermal expansion differential between the glaze and the refractory body; and
    e2) subtracting the thermal expansion differential from the coefficient of thermal expansion of the glaze to yield the coefficient of thermal expansion of the refractory body.

6. The method of claim 4 wherein step a) further comprises applying a series of glazes, each characterized by a unique coefficient of thermal expansion, to the refractory body.

7. The method of claim 4 wherein step e) further includes comparing the average crack-to-crack distance in the crazed glaze to tabulated values of average crack-to-crack distance versus refractory body thermal expansion coefficients to differentials for glazes of known values at known firing temperatures to extrapolate the coefficient of thermal expansion of the refractory body.

8. The method of claim 4 wherein step e) includes calculating the coefficient of thermal expansion of the refractory body from the coefficient of thermal expansion of the glaze, the firing temperature, and the average crack-to-crack distance.

9. The method of claim 4 wherein step c) includes cooling the glazed body substantially from the firing temperature to a predetermined crazing temperature at a predetermined cooling rate.

10. The method of claim 1, wherein the glaze has an unknown coefficient of thermal expansion and the refractory body has a known refractory body coefficient of thermal expansion; and wherein step c) includes firing the glazed body to as first predetermined temperature.

11. The method of claim 10 wherein step e) further includes the substeps of:
   e1) determining the thermal expansion differential between the glaze and the refractory body; and
   e2) adding the thermal expansion differential to the coefficient of thermal expansion of the refractory body to yield the coefficient of thermal expansion of the glaze.

12. The method of claim 10 wherein step a) further comprises applying the glaze to a series of refractory bodies, each respectively characterized by a unique coefficient of thermal expansion.

13. The method of claim 10 wherein step e) further includes comparing the average crack-to-crack distance in the crazed glaze to tabulated values of average crack-to-crack distance versus glaze thermal expansion coefficients to differentials for refractory bodies of known values at known firing temperatures to extrapolate the coefficient of thermal expansion of the glaze.

14. The method of claim 10 wherein step e) includes calculating the coefficient of thermal expansion of the glaze from the coefficient of thermal expansion of the refractory body, the firing temperature, and the average crack-to-crack distance.

15. A method of determining the coefficient of thermal expansion of a glaze or refractory body, comprising:
   a) applying a glaze to a refractory body to yield a glazed body, wherein the glaze and the refractory body are each characterized by a respective coefficient of thermal expansion, wherein the glaze is characterized by a known elastic modulus, wherein the glaze is characterized by a known failure stress, wherein the glaze is characterized by a known glass transition temperature, wherein one of the respective coefficients of thermal expansion is known and the other respective coefficient of thermal expansion is unknown;
   b) firing the glazed body to as first predetermined temperature;
   c) crazing the glaze on the glazed body to create cracks;
   d) measuring the average distance between cracks in the crazed glaze; and
   e) determining the unknown coefficient of thermal expansion by using the relation between the coefficient of thermal expansion of the glaze, the coefficient of thermal expansion of the refractory body, the failure stress of the glaze, the elastic modulus of the glaze, the glass transition temperature of the glaze, ambient temperature after cooling and the average distance between of the cracks in the crazed glaze.

16. The method of claim 15 wherein step c) includes cooling the glazed body substantially from the firing temperature to a predetermined crazing temperature at a predetermined cooling rate.

17. The method of claim 15 wherein step e) includes calculating the coefficient of thermal expansion of the refractory body from the coefficient of thermal expansion of the glaze, the firing temperature, and the average crack-to-crack distance.

18. The method of claim 15 wherein step e) includes calculating the coefficient of thermal expansion of the glaze from the coefficient of thermal expansion of the refractory body, the firing temperature, and the average crack-to-crack distance.

19. A method of determining the coefficient of thermal expansion of a glaze or a refractory body, comprising:
   a) applying a glaze to a refractory body to yield a glazed body, wherein the glaze and the refractory body are each characterized by a respective coefficient of thermal expansion, wherein one of the respective coefficients of thermal expansion is known and the other respective coefficient of thermal expansion is unknown;
   b) firing the glazed body to as first predetermined temperature;
   c) crazing the glaze on the glazed body and creating cracks;
   d) recording the average distance between cracks in the crazed glaze; and
   e) determining the unknown coefficient of thermal expansion from the average distance between cracks in the crazed glaze, the firing temperature, and the known coefficient of thermal expansion.

20. The method of claim 19 wherein step e) includes a calculation.

21. The method of claim 19 wherein step e) includes reference to tabulated data.

* * * * *